US007864041B2

(12) United States Patent
Godlewski

(10) Patent No.: US 7,864,041 B2
(45) Date of Patent: Jan. 4, 2011

(54) ACTIVE-TAG BASED DISPENSING

(75) Inventor: Peter Phillip Godlewski, San Clemente, CA (US)

(73) Assignee: Carefusion 303, Inc., San Diego, CA (US)

(*) Notice: Subject to any disclaimer, the term of this patent is extended or adjusted under 35 U.S.C. 154(b) by 469 days.

(21) Appl. No.: 11/946,698

(22) Filed: Nov. 28, 2007

(65) Prior Publication Data

US 2009/0134997 A1    May 28, 2009

(51) Int. Cl.
*G08B 1/08* (2006.01)
(52) U.S. Cl. .............. 340/539.1; 340/572.1; 340/572.4; 705/22
(58) Field of Classification Search .............. 340/539.1, 340/572.1–572.9; 705/28, 22, 23, 24, 225
See application file for complete search history.

(56) References Cited

U.S. PATENT DOCUMENTS

| 6,903,656 | B1 | 6/2005 | Lee |
| 7,183,920 | B2* | 2/2007 | Napolitano .............. 340/572.1 |
| 7,406,439 | B2* | 7/2008 | Bodin et al. .................. 705/22 |
| 2003/0144926 | A1 | 7/2003 | Bodin et al. |
| 2005/0171738 | A1 | 8/2005 | Kadaba |
| 2005/0231365 | A1 | 10/2005 | Tester et al. |
| 2007/0138272 | A1 | 6/2007 | Saperstein et al. |
| 2007/0268138 | A1 | 11/2007 | Chung et al. |

FOREIGN PATENT DOCUMENTS

EP    1 793 326 A2    6/2007

OTHER PUBLICATIONS

PCT International Search Report/Written Opinion for International Application No. PCT/US2008/084582 dated Mar. 10, 2009.

* cited by examiner

*Primary Examiner*—Anh V La
(74) *Attorney, Agent, or Firm*—McDermott Will & Emery LLP

(57) ABSTRACT

A method of sensing dispensation of a product from a storage device having an antenna is provided. The method comprises providing a product with a wireless tag within a service area of the antenna, establishing wireless communication between the wireless tag and the antenna, monitoring the wireless communication, and determining, responsive to the monitoring, when the wireless communication has ceased to establish when the product has been dispensed from the storage device. A dispensation-sensing system is also provided. The system comprises a securable storage area, an antenna operable to receive and transmit signals within the securable storage area, and a processor. The processor is configured to establish wireless communication between the antenna and a wireless tag of a product disposed within the securable storage area, monitor the wireless communication, and determine, responsive to the monitoring, when the wireless communication has ceased to establish when the product has been dispensed from the securable storage area.

26 Claims, 9 Drawing Sheets

ACTIVE-TAG BASED DISPENSING

CROSS-REFERENCE TO RELATED APPLICATION

Not applicable.

STATEMENT REGARDING FEDERALLY SPONSORED RESEARCH OR DEVELOPMENT

Not applicable.

FIELD

Embodiments of the present invention generally relate to dispensation of products and, in particular, relate to active tag-based dispensing.

BACKGROUND

Centralized inventory systems are frequently used in the medical community to track and dispense medical products such as medications, medical devices, etc. Some of these items may be sophisticated and expensive instruments, and keeping close track of these items is desirable from a caregiver viewpoint as well as an ownership viewpoint. For a caregiver, it is important to be able to quickly and accurately locate a needed item. As an owner of the facility, it is important that very expensive items, such as electronic instruments, be protected from theft to the extent possible.

In such a centralized inventory system, medical products are stored in a storage area, such as a wall cabinet or other secure location. The dispensation of the products from the storage area may be tracked by requiring authorized users to indicate in a tracking log which products, and what quantity thereof, they have removed from the storage area. Similarly, low-stock and out-of-stock warnings may be provided by an alert user who notes the dwindling supply of a product as he removes it. These systems, however, rely upon the compliance of the users to track the dispensation of products therefrom, and are therefore prone to error.

SUMMARY

Embodiments described herein address the foregoing problems by tracking the dispensation of products from storage areas with wireless tags. As user compliance is not required to track the dispensation of products, the accuracy and efficacy of the dispensation tracking is improved. Moreover, as an accurate inventory can be reliably and automatically maintained, automated inventory warnings can be generated when warranted. Additional features include the ability to track environmental information associated with individual products (e.g., product age, exposure to damaging conditions such as heat or radiation, location history, etc.).

Certain embodiments provide a method of sensing dispensation of a product from a storage device having an antenna. The method comprises the steps of providing a first product with a first wireless tag within a service area of the antenna, establishing wireless communication between the first wireless tag and the antenna, monitoring the wireless communication, and determining, responsive to the monitoring, when the wireless communication has ceased to establish when the first product has been dispensed from the storage device.

Certain embodiments provide a method of sensing dispensation of a product from a storage device having an antenna. The method comprises the step of providing a plurality of products within a service area of the antenna. Each of the plurality of products includes a wireless tag. The method further comprises the steps of establishing a first wireless link between the antenna and at least one of the plurality of wireless tags, and establishing a plurality of second wireless links between the plurality of wireless tags, the plurality of second wireless links being coupled to the first wireless link. The method further comprises the steps of monitoring the first wireless link and the plurality of second wireless links, and determining, responsive to the monitoring, when one of the plurality of second wireless links has been lost to establish when a corresponding one of the plurality of products has been dispensed from the storage device.

Certain embodiments provide a dispensation-sensing system. The system comprises a securable storage area, an antenna operable to receive and transmit signals within the securable storage area, and a processor. The processor is configured to establish wireless communication between the antenna and a first wireless tag of a first product disposed within the securable storage area, monitor the wireless communication, and determine, responsive to the monitoring, when the wireless communication has ceased to establish when the first product has been dispensed from the securable storage area.

It is to be understood that both the foregoing summary and the following detailed description are exemplary and explanatory and are intended to provide further explanation of the embodiments as claimed.

BRIEF DESCRIPTION OF THE DRAWINGS

The accompanying drawings, which are included to provide further understanding of the invention and are incorporated in and constitute a part of this specification, illustrate embodiments of the invention and together with the description serve to explain the principles of the invention. In the drawings.

DETAILED DESCRIPTION

In the following detailed description, numerous specific details are set forth to provide a full understanding of the disclosed and claimed embodiments. It will be apparent, however, to one ordinarily skilled in the art that the embodiments may be practiced without some of these specific details. In other instances, well-known structures and techniques have not been shown in detail to avoid unnecessarily obscuring the disclosure.

Maintaining an accurate inventory of medical products (e.g., medications, medical devices, biological samples, donated organs, etc.) is an important part of providing exemplary patient care. Accordingly, certain embodiments provide accurate, automated methods and systems for tracking the dispensation of medical products from their respective storage devices (e.g., cabinets, stock rooms, drawers, etc.). In addition to tracking the dispensation of products, certain embodiments can also perform inventory tracking, associate authorized users with the products they dispense, and maintain a database of product information.

Figure 1A:
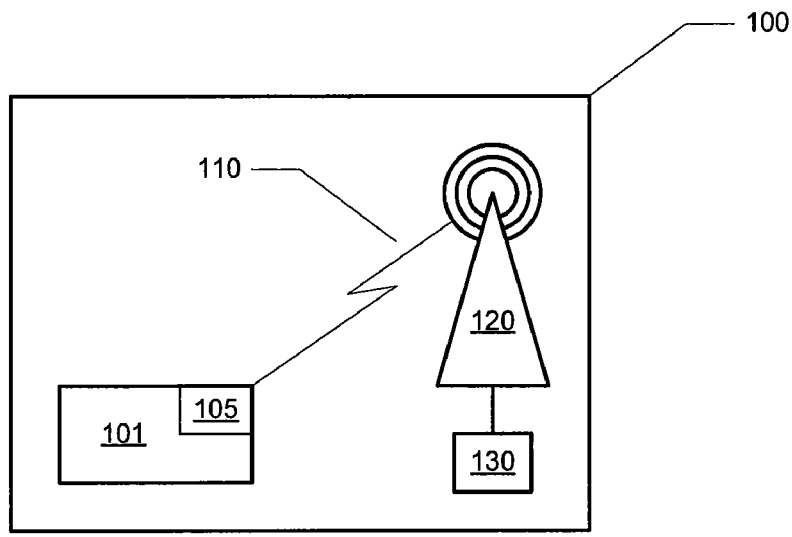
FIG. 1a is a block diagram illustrating a dispensation-sensing system in accordance with certain embodiments.

For example, FIG. 1a is a block diagram illustrating a dispensation-sensing system in accordance with certain embodiments. The system includes a securable storage area 100, together with an antenna 120 that can transmit and receive signals within storage area 100, and a processor 130 operably coupled to antenna 120. Storage area 100 may be, for example, a locked drawer, cabinet or even an entire stock room, in which medical products are stored. According to one aspect, the boundaries of storage area 100 may be determined by the effective range of antenna 120 (e.g., because the walls thereof reduce the signal strength of antenna 120 below an effective threshold). Alternatively, the boundaries of storage area 100 may be narrower or larger than the effective range of antenna 120.

Disposed within storage area 100 is a medical product 101. Medical product 101 may be, for example, a medication, a medical device such as a syringe, a medical instrument such as an infusion pump, or any one of a number of other medical products for which reliable dispensation tracking is desired. Included on medical product 101 is a wireless tag 105. Wireless tag 105 may be, for example, an active RFID tag. Active RFID tags are well known to those of skill in the art, in part because of their relatively low cost, their small size, and the ease with which they can be integrated into various types of packaging.

Figure 1B:
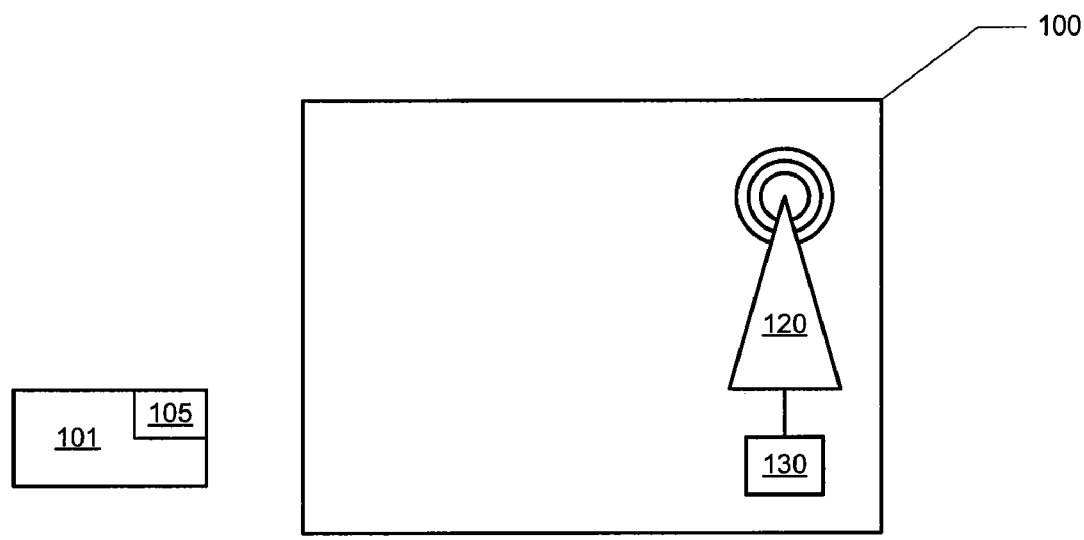
FIG. 1b is a block diagram illustrating a dispensation-sensing system in accordance with certain embodiments.

Processor 130 is configured to establish and maintain a wireless link 110 between antenna 120 and wireless tag 105 on medical product 101. Processor 130 monitors the wireless link 110, either continuously or at periodic intervals, to determine whether medical product 101 is still within the range of antenna 120 (i.e., whether medical product 101 is still within storage area 100). Once medical product 101 has been removed from the storage area, as illustrated in FIG. 1b, wireless link 110 is lost (e.g., because wireless tag 105 of medical product 101 is outside the effective range of antenna 120). Processor 130, which has been monitoring wireless link 110, determines that wireless link 110 has been lost, and accordingly establishes that medical product 101 has been dispensed. Processor 130 may also be provided with a clock or access to a timing signal, whereby processor 130 can determine at what time medical product 101 was dispensed, and can record the event in a memory or external database (as described in greater detail below).

While the wireless tag of the present exemplary embodiment has been described as an active RFID tag, the scope of the present invention is not limited to this particular arrangement. Rather, as will be readily apparent to those of skill in the art, any one of a number of different wireless tags may be used, including, for example, semi-passive RFID tags, RuBee tags, Bluetooth™ tags, or near field communication ("NFC") tags.

Figure 2A:
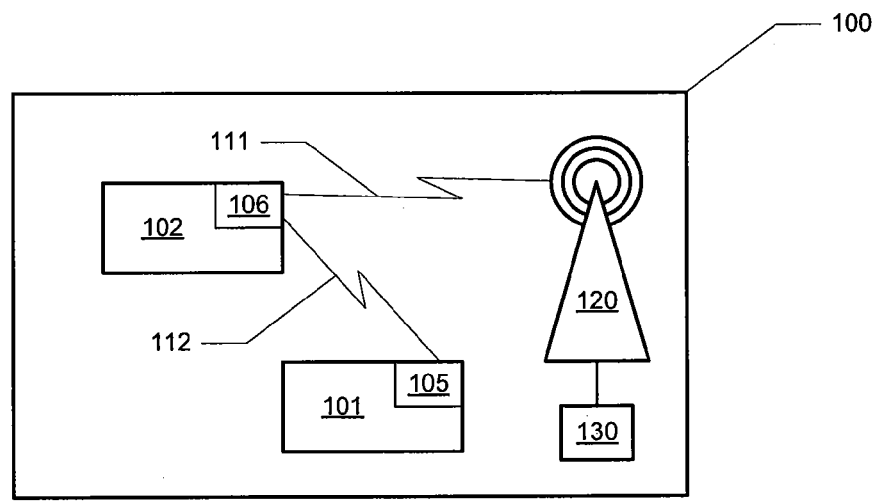
FIG. 2a is a block diagram illustrating a dispensation-sensing system in accordance with certain embodiments.
Figure 2B:
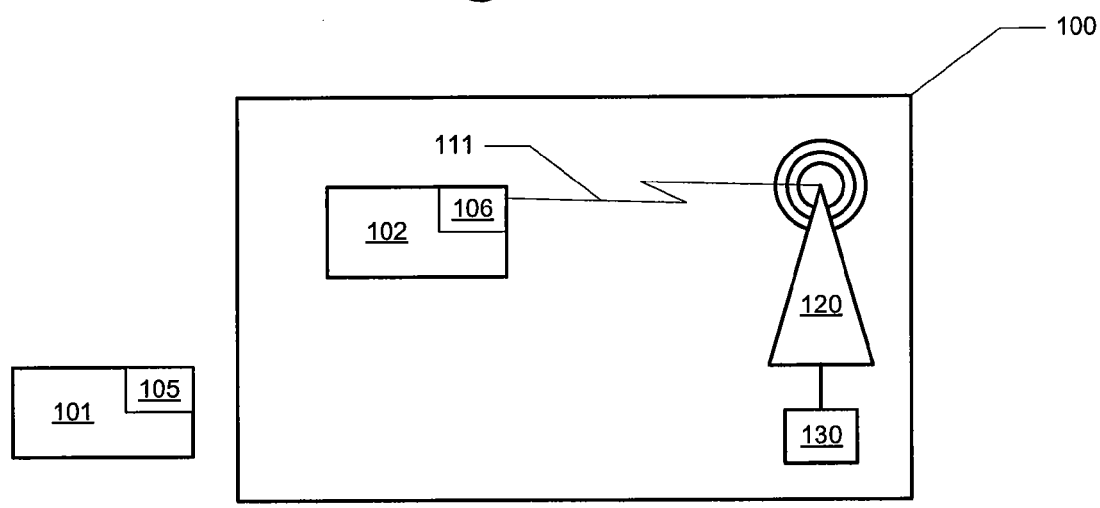
FIG. 2b is a block diagram illustrating a dispensation-sensing system in accordance with certain embodiments.

In accordance with certain embodiments, the wireless link monitored by processor 130 need not be a direct link between antenna 120 and wireless tag 105 of medical product 101. For example, FIG. 2a is a block diagram illustrating a dispensation-sensing system in accordance with certain embodiments, in which multiple medical products are disposed within the system. As can be seen with reference to FIG. 2a, medical products 101 and 102 are disposed within the storage area 100 of the system. Antenna 120 has established a wireless link 111 with a wireless tag 106 of medical product 102. Another wireless link 112 has been established between wireless tag 106 of medical product 102 and wireless tag 105 of medical product 101. Wireless tag 106 of medical product 102 is configured to relay information about wireless link 112 to antenna 120 over wireless link 111. Accordingly, processor 130 is able to monitor both wireless link 112 and wireless link 111. In this manner, when medical product 101 is removed from storage area 100, as illustrated in FIG. 2b, processor 130 is able to determine when wireless link 112 is lost, and thereby establish when medical product 102 has been dispensed from storage area 100.

Alternatively, if medical product 102 had been dispensed from storage area 100, in lieu of medical product 101 (as has been illustrated in FIG. 2b), both wireless links 111 and 112 would have been lost, at least temporarily. In this scenario, wireless tag 105, which is configured to continually seek to establish wireless links with either antennas such antenna 120 or other similarly configured wireless tags, would have quickly established a new wireless link with antenna 120, resulting in the configuration illustrated in FIG. 1a. Thus, while processor 130 may have determined, while monitoring the wireless links, that wireless link 111 had been lost, a new wireless link (e.g., like wireless link 110 in FIG. 1a) would have been established within a time period less than a predetermined threshold, and processor 130 would not therefore determine medical product 101 to have been dispensed.

In certain embodiments, wireless tags such as wireless tags 105 and 106 may communicate with each other and with antenna 120 over a single frequency. In other embodiments, wireless tags 105 and 106 may communicate with each other on a first frequency, and communicate with antenna 120 on a second frequency. For example, in the embodiment illustrated in FIG. 2a, wireless tag 106 may communicate with antenna 120 on a higher frequency (e.g., one with a greater range or better reliability) than the frequency with which wireless tags 105 and 106 communicate. Such an arrangement may provide a more robust connection between wireless tag 106 and antenna 120, to ensure that the information about product 101, which is relayed by wireless tag 106, reaches antenna 120. A lower frequency (e.g., one which consumes less battery power) may be utilized to communicate between wireless tags, as each wireless tag in a storage area need not communicate with every other wireless tag, but only those which are relatively close (as will be discussed in greater detail below).

In certain embodiments, groups of medical products disposed within the same storage device form spontaneous "mesh networks" (e.g., networks for which no additional infrastructure beyond the wireless tags is necessary) that can connect wirelessly with the antenna of the dispensation-sensing system. The mesh network can be considered to be at least partially self-aware, in the sense that the presence of each wireless tag is "known" to one or more nearby wireless tags with which it has formed wireless links. Accordingly, when one wireless tag (attached to a medical product) goes missing from the mesh network (e.g., because it has been dispensed from the storage area), the mesh network will be able to communicate that information to the antenna of the dispensation-sensing system. Accordingly, the antenna need not be directly connected to (i.e., need not form wireless links with) each wireless tag in the storage area.

Figure 3:
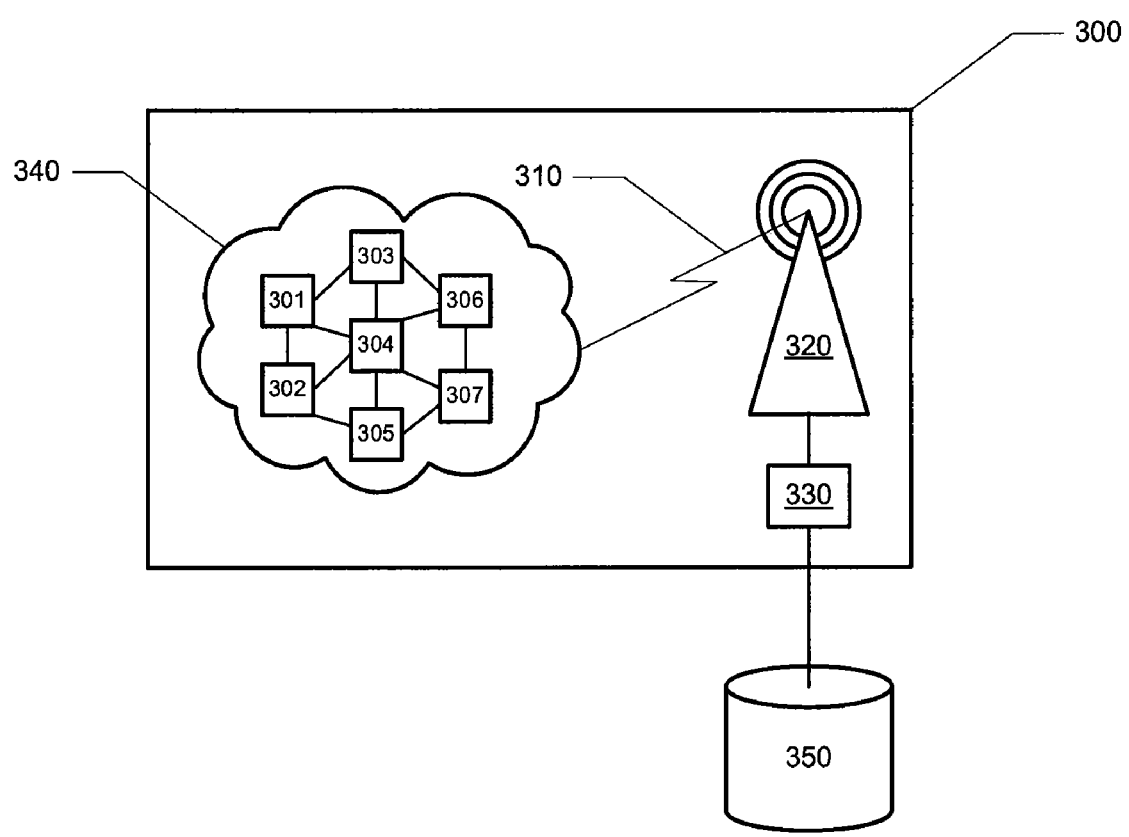
FIG. 3 is a block diagram illustrating a dispensation-sensing system in accordance with certain embodiments.

This concept is illustrated in FIG. 3, in which a block diagram of a dispensation-sensing system is shown in accordance with certain embodiments. The dispensation-sensing system includes a storage area 300, an antenna 320 operable within storage area 300, and a processor 330 operably coupled to antenna 320. A plurality of medical products 301-307 have established a mesh network 340, as described above, by forming a number of wireless links amongst the wireless tags thereof. For clarity of illustration, the wireless tags of medical products 301-307 are not schematically illustrated in FIG. 3. Antenna 320 is connected to mesh network 340 via one or more wireless links, such as wireless link 310. Processor 330 may monitor mesh network 340 through antenna 320 in a number of ways, including, for example, regularly polling the wireless tags to which antenna 320 is connected to determine which wireless tags they are connected to, etc. When one or more of the medical products 301-307 is removed from the mesh network (e.g., because it has been dispensed), processor 330 will detect their absence, by comparing an updated list of wireless tags determined in the most recent polling iteration with a previous list of wireless tags from a previous polling iteration. In a similar manner, processor 330 will detect the addition of new wireless tags (and their associated medical products) to mesh network 340.

In accordance with certain embodiments, antenna 320 may be configured to periodically operate at a higher broadcast power, to temporarily form separate wireless links with each of the wireless tags on medical products 301-307, to verify that mesh network 340 is accurately reporting the presence of all wireless tags therein, and not inadvertently reporting the presence of a wireless tag that has already been dispensed.

The dispensation-sensing system of FIG. 3 is operably coupled to a database 350. As will be readily apparent to those of skill in the art, this configuration permits the system to share information regarding the dispensation of medical products from storage area 300 with database 350, and create a centralized inventory tracking system. According to certain embodiments, each wireless tag may be associated with a unique identification number, permitting a single medical product to which the tag is attached to be tracked from system to system (e.g., in a hospital environment in which many dispensation systems are operably coupled with the same database, over, for example, a network connection). Connecting the system with database 350 allows the system to share other information about medical products 301-307 with database 350 as well, as is discussed in greater detail below.

According to certain aspects, processor 330 may be configured to generate low-stock or out-of-stock warnings when the stock of a particular medical product in storage area 300 reaches a predetermined threshold. This warning may be provided to a remote user over a network connection such as, for example, the network connection utilized to operably couple the dispensation-sensing system to database 350. Alternatively, database 350 may be connected to a separate processor or other computing device which is configured to generate similar warnings based on the stock levels of various medical products reported by dispensation-sensing systems to database 350.

Figure 4A:
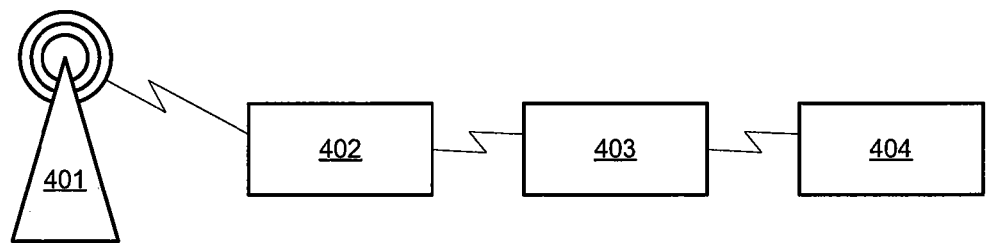
FIG. 4a is a block diagram illustrating a network of wireless tags in accordance with certain embodiments.
Figure 4B:
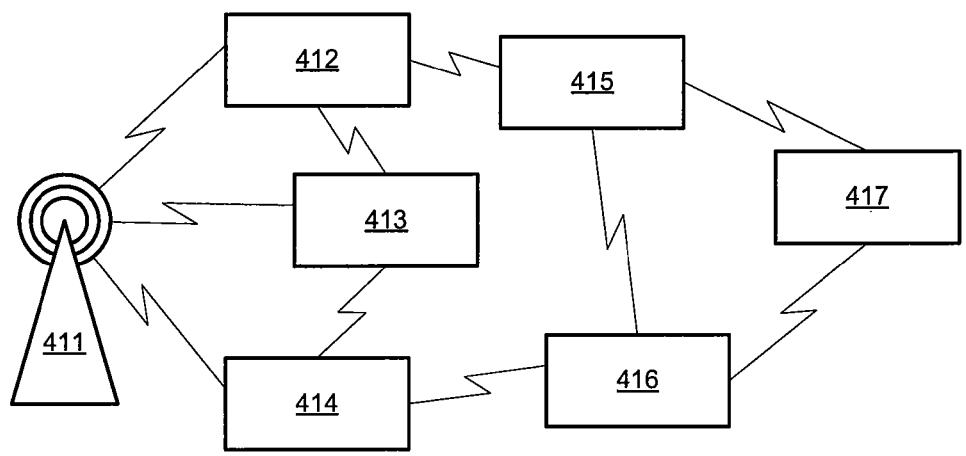
FIG. 4b is a block diagram illustrating a network of wireless tags in accordance with certain embodiments.

A mesh network may have any one of a number of network topologies. For example, FIGS. 4a and 4b illustrate two possible network topologies. In FIG. 4a, a network of three wireless tags 402-404 is connected to an antenna 401. In this network configuration, antenna 401 is configured to form and maintain one wireless link (i.e., the wireless link between antenna 401 and wireless tag 402), and each wireless tag 402-404 is configured to form and maintain two wireless links (e.g., wireless tag 402 forms a link with antenna 401 and a link with wireless tag 403, wireless tag 403 forms a link with wireless tag 402 and wireless tag 404). Accordingly, this network topology can be envisioned as a "chain" topology. As can be seen with reference to FIG. 4a, the last "link" in the chain, wireless tag 404, can only form one wireless link (i.e., with wireless tag 403), as no further wireless tags are in its vicinity. This configuration ensures that wireless tag 404 will periodically poll its vicinity to determine if another wireless tag has come within range. Because wireless tags 402-404 are configured to collect and share information concerning the mesh network that they have formed, as soon as wireless tag 404 forms another wireless link (e.g., with a newly added wireless tag), that information will be relayed through wireless tags 403 and 402, in turn, to antenna 401 (and from antenna 401 to an associated processor, as described in greater detail above).

Turning to FIG. 4b, another network of wireless tags is illustrated in accordance with certain embodiments. In the network topology of FIG. 4b, each of antenna 411 and wireless tags 412-417 are configured to form and maintain three wireless links. Accordingly, when a wireless tag is added to or removed from the mesh network, this information will have several possible routes to antenna 411 (and its associated processor), rendering the network more robust, albeit at the cost of greater power consumption (and concomitant shorter battery life) in the wireless tags.

According to one aspect, a mesh network, such as is illustrated in FIG. 4b, can maintain information not only about the identity of wireless tags in the network, but about the relationship of those tags (e.g., information about which tags share links). This information about the topology of the network solves an additional problem common to wireless tag-based product dispensing, in which a user can "cheat" a dispensation system by removing a product from its packaging, and replacing the packaging, with the wireless tag, into the system. By so doing, the user can fool the system into believing that the inventory has not changed (as the tag is still registered as present). With a mesh network that maintains topology information, however, removing a product (even temporarily) will cause the links of that product's wireless tag to be removed from the mesh network, and replaced elsewhere in the topology (when the empty packaging is returned). If during a subsequent inspection an empty package is discovered, the system can identify the user associated with the change in topology of the empty packaging. In this way, a mesh style topology addresses the problem of "spoofing" a dispensation system by removing the product, but not the tag, from the system.

In accordance with certain embodiments, wireless tags 412-417 may communicate with one another at frequency that requires less power (e.g., and which has a smaller range) than the frequency with which the network communicates with antenna 411 (e.g., via wireless tags 412-414). According to such an embodiment, each wireless tag only needs to have an effective range of communication that encompasses some of its neighbors. For example, wireless tag 417 need not broadcast and receive with sufficient power to form a wireless link directly with wireless tag 412, which is located at some distance from wireless tag 417. Rather, wireless tag 417 may utilize a lower-power frequency to communicate directly only with wireless tags 415 and 416. To ensure a robust connection between the network and antenna 411, however, wireless tags 412-414 may utilize a higher-power frequency to maintain wireless links with antenna 411. In another arrangement, all of wireless tags 412-417 and antenna 411 may utilize the same frequency, but wireless tags 412-417 may utilize different power levels (e.g., via greater or lesser amplification) depending upon whether they are communicating with antenna 411 or another wireless tag.

While the foregoing exemplary embodiments have described two particular network topologies, the scope of the present invention is not limited to these particular configurations. As will be readily apparent to those of skill in the art, any one of a number of network topologies, or any combination thereof, may be utilized in a mesh network of wireless tags.

Figure 5:
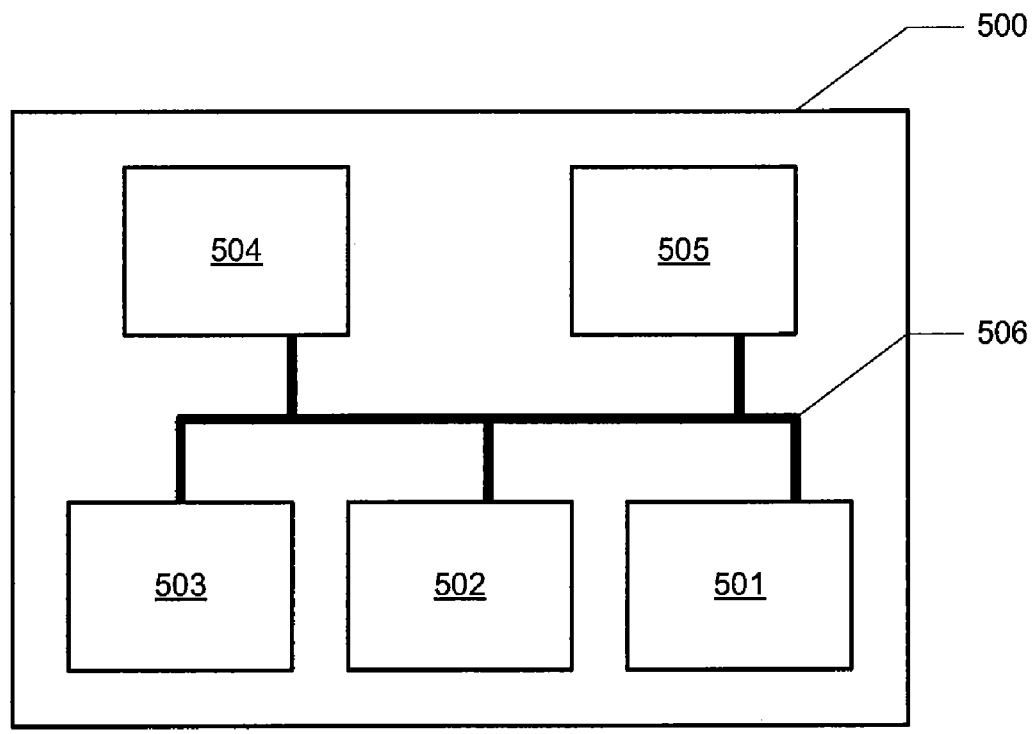
FIG. 5 is a block diagram illustrating a wireless tag in accordance with certain embodiments.

A wireless tag that is attached to a medical product may provide additional functionality beyond assisting in the sensing and tracking of dispensation of the medical product from a storage device. For example, the wireless tag may be able to sense environmental factors that could impact the medical product to which it is attached (e.g., heat, radiation, humidity, moisture, chemical exposure, etc.), and report those environmental factors to a dispensation-sensing system. For example, FIG. 5 illustrates a wireless tag 500 in accordance with certain embodiments. Wireless tag 500 includes an antenna 501 for communicating with the antenna of a dispensation system and with the antennas of other wireless tags. A processor 502 is also provided, to control antenna 501 and to retrieve information from and store information in memory 503. The information stored in memory 503 may be obtained from antenna 501 (e.g., information about other wireless tags in range, information about the storage area in which wireless tag 500 is disposed, etc.), or may alternately be obtained by environmental sensor 504. Memory 503 may also store program code for execution by processor 502, which configures wireless tag 500 to form mesh networks, communicate with dispensation-sensing systems, measure environmental information, etc. A bus 506 is used to connect antenna 501, processor 502, memory 503 and environmental sensor, and a battery 505 is included to provide power to wireless tag 500. In certain embodiments, battery 505 may be replaceable and/or rechargeable.

Environmental sensor 504 may be configured to sense many different environmental parameters of interest. For example, environmental sensor 504 may be configured to measure ambient temperature, to inform when a medication to which wireless tag 500 is attached has been denatured or otherwise compromised by excess heat. Environmental sensor 504 may alternately be configured to measure the ambient humidity, to similarly inform when the medical product attached to wireless tag 500 has been compromised by excess moisture. With this information, administrative personnel may be able to correct environmental hazards (such as excess moisture and heat) in a storage area in time to prevent other medical products from becoming similarly compromised.

While wireless tag 500 has been illustrated as including a single environmental sensor, the scope of the present invention is not limited to this particular arrangement. Rather, any number of environmental sensors may be included on a wireless tag. Some wireless tags may not be provided with any wireless sensors at all, others may have multiple environmental sensors, and still others may have multiple redundant sensors (e.g., more than one sensor configured to measure temperature) to ensure the accuracy thereof.

Attaching a wireless tag such as wireless tag 500 to a medical product presents a challenge: if the wireless tag is not securely attached to the medical product, it may either accidentally or intentionally be removed prematurely (e.g., before medical product is consumed or otherwise used), and thereby foil the dispensation-sensing systems. Some methods of securely attaching a wireless tag to a medical product, however, might require compromising the sterile packaging thereof, an equally unacceptable solution. Accordingly, an environmental sensor of a wireless tag may be configured to measure the attachment status of a wireless tag to a medical product (e.g., by maintaining electrical contact with a metal conductor of a medical product, or by depressing a pressure switch, etc.). Should the wireless tag sense that it is no longer attached to the medical product, it can provide this information to a dispensation-sensing system. Thus, should a user seek to remove a medical product from a dispensation-sensing system without alerting the system, the wireless tag will report its removal from the medical product, and associate the last user with access to the storage area with the removal. In this way, the wireless tag can be secured to a medical product without compromising the sterile packing thereof, while mitigating the risk of removal therefrom. In this manner, attachment status can be considered another type of environmental information collected by and stored in wireless tag 500.

The environmental information collected by wireless tag 500 can be communicated to a database operably coupled to a dispensation-sensing system, via either a direct link between wireless tag 500 and the antenna of the system, or via a mesh network of wireless tags which relays the information to the system. Other information that wireless tag 500 can track and relay to the database may include the location of the last storage area in which the wireless tag was disposed, the duration of the last storage period, etc. This level of environmental information tracking can provide a comprehensive database of inventory health, location, and access, which, as will be readily apparent to those of skill in the art, can be of great advantage to a hospital administrator or other care provider.

According to certain embodiments, a wireless tag such as wireless tag 500 may be reusable once the product to which it is attached has been consumed and/or removed. In such an embodiment, once wireless tag 500 is removed from the product, it can be provided with a signal to execute code stored in memory 503 to re-initialize the tag (e.g., to clear memory 503 of stored environmental information, to optionally generate a new unique identification number, etc.). The ability to reuse wireless tags adds significant value to the dispensation-sensing systems, as no part of the system need be consumable or exhaustible.

Figure 6:
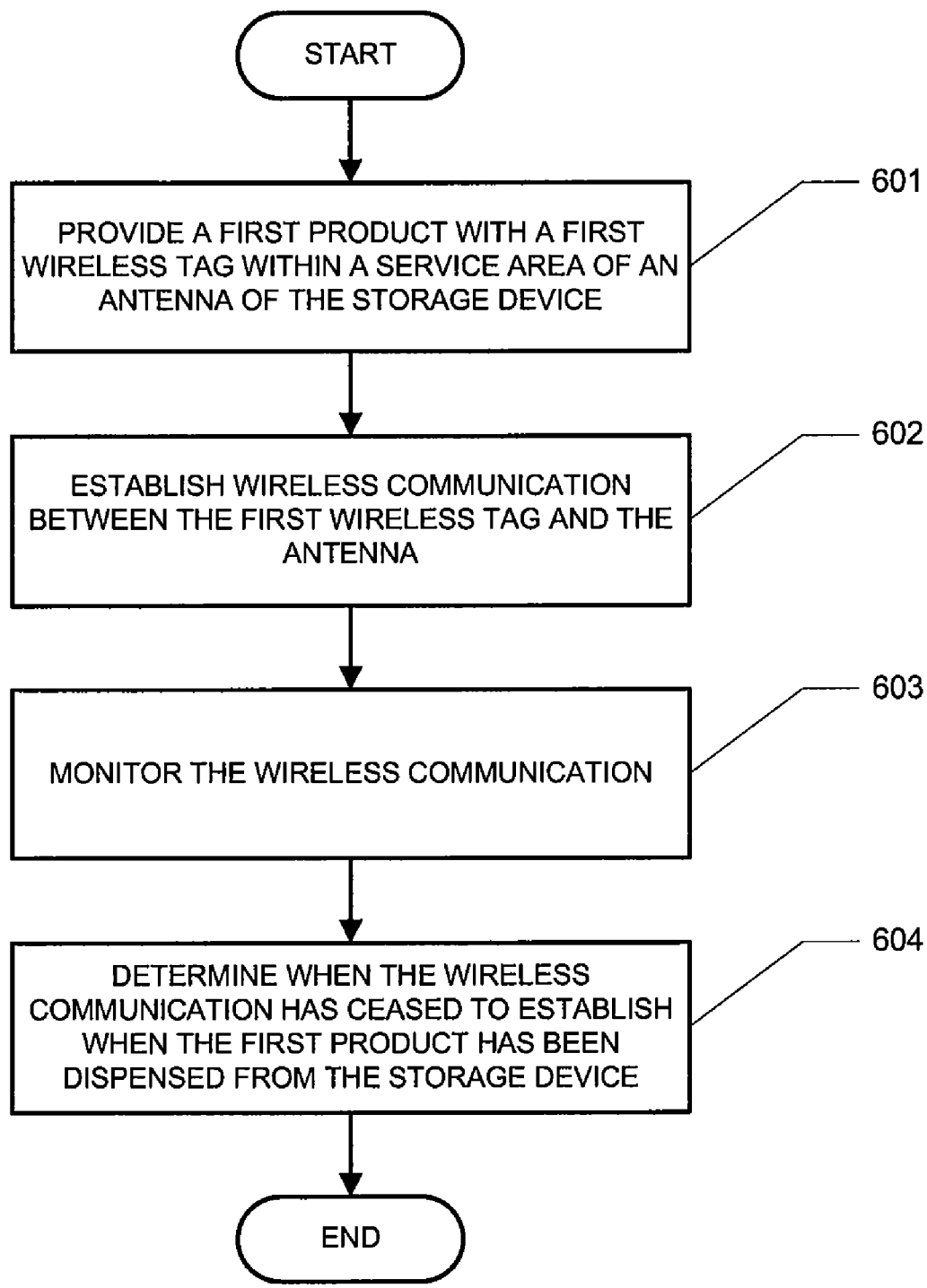
FIG. 6 is a flow chart illustrating a method of sensing dispensation of a product from a storage device in accordance with certain embodiments.

FIG. 6 is a flow chart illustrating a method of sensing dispensation of a product from a storage device in accordance with certain embodiments. The method begins with step 601, in which a product with a wireless tag is provided within the service area of an antenna of a storage device. In step 602, wireless communication is established between the wireless tag and the antenna of the storage device. In step 603, the wireless communication is monitored to determine, in step 604, when the wireless communication has ceased, to establish when the product has been dispensed from the storage device.

Figure 7:
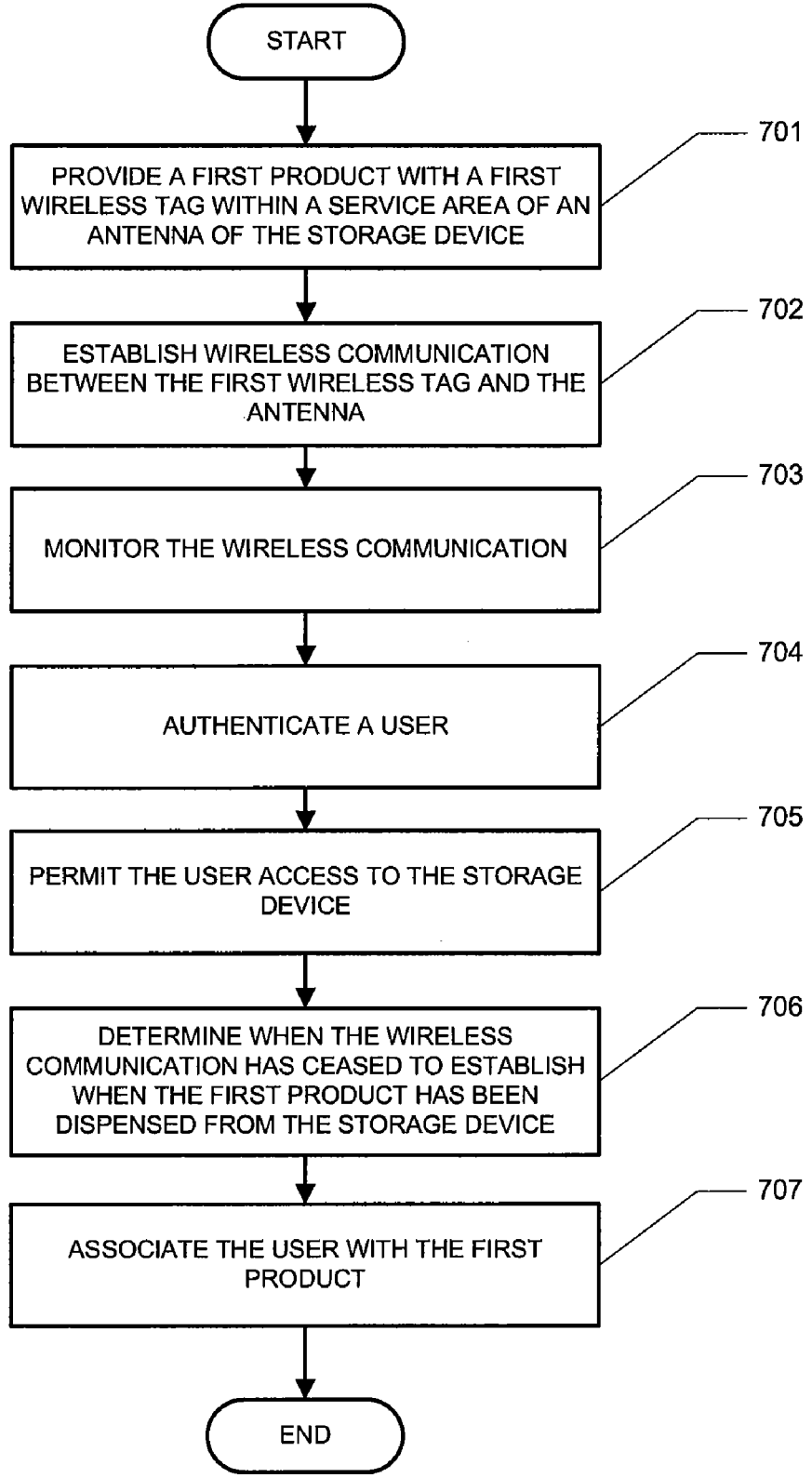
FIG. 7 is a flow chart illustrating a method of sensing dispensation of a product from a storage device in accordance with certain embodiments.

According to another aspect, a method of sensing dispensation may also track the users responsible for the dispensation of medical products from a storage area. For example, FIG. 7 is a flow chart illustrating a method of sensing dispensation of a product from a storage device in accordance with certain embodiments. The method begins with step 701, in which a product with a wireless tag is provided within the service area of an antenna of a storage device. In step 702, wireless communication is established between the wireless tag and the antenna of the storage device. In step 703, the wireless communication is monitored. In step 704, a user is authenticated, and permitted, in step 705, to access the storage device. In 706, responsive to the monitoring of step 703, a determination is made when the wireless communication ceases to establish when the product has been dispensed from the storage device. In step 707, the user authenticated in step 704 is associated with the product dispensed in step 706.

In embodiments in which the dispensation-sensing system is operably coupled to a database, the association of the user with the product of step 707 may take the form of an entry in the database, including the unique identification number of the wireless tag of the dispensed product, the time it was dispensed, an identification of which dispensation-sensing system it was dispensed from, and by which authorized user. In certain embodiments, additional information may further be associated with the dispensation, such as environmental information collected by the wireless tag, etc. Tracking this information from a networked database renders the tracking of medical products, and supervision of authorized users, from any computing device with access to the database, and greatly simplifies the task of hospital administration.

Figure 8:
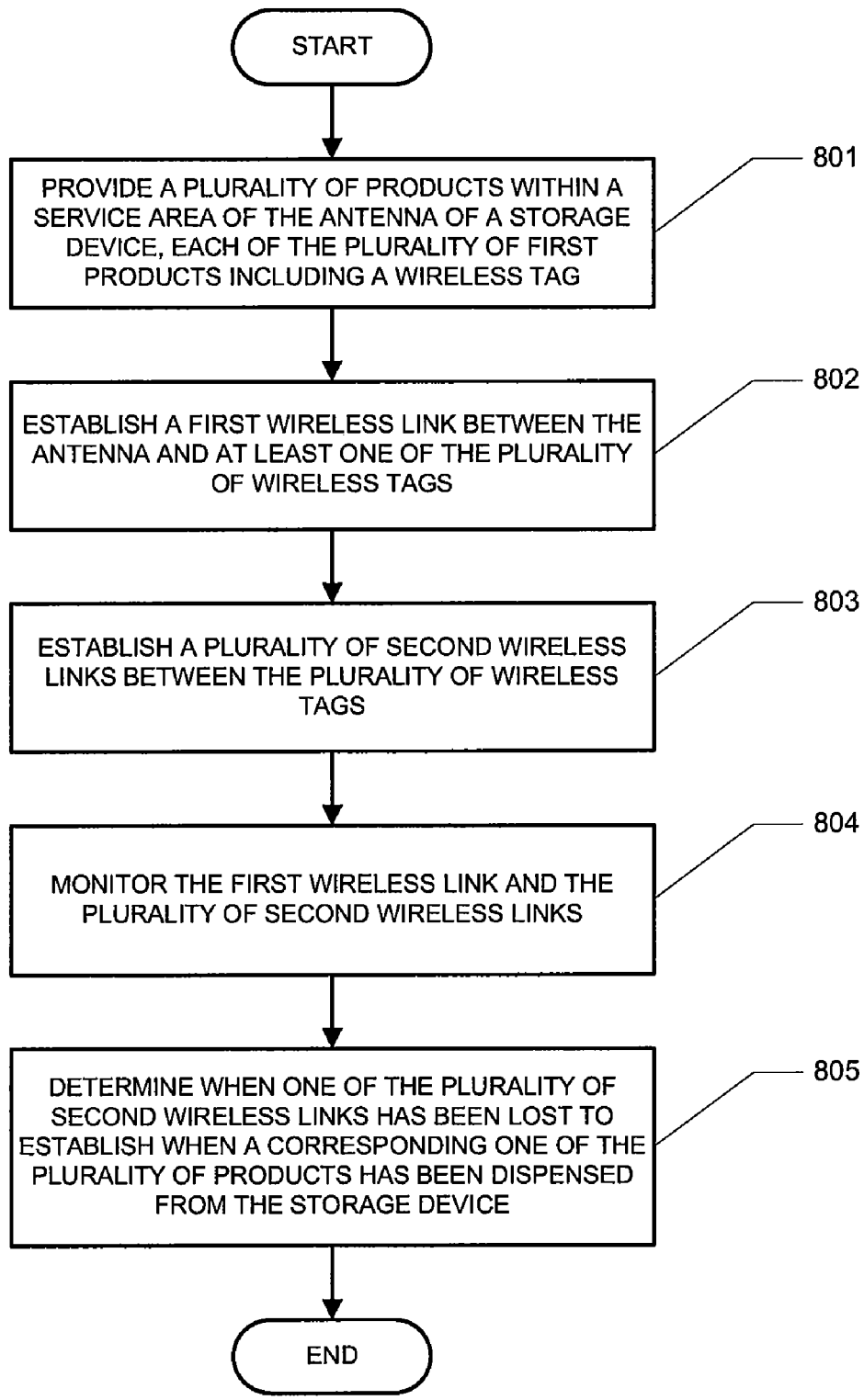
FIG. 8 is a flow chart illustrating a method of sensing dispensation of a product from a storage device in accordance with certain embodiments.

FIG. 8 is a flow chart that illustrates a method of sensing dispensation of a product from a storage device in accordance with certain embodiments. The method begins with step 801 in which a plurality of products are provided within the service area of an antenna of a storage device. Each of the plurality of first products includes a wireless tag. In step 802, a first wireless link is established between the antenna and at least one of the plurality of wireless tags. The method continues in step 803, in which a plurality of second wireless links are established between the plurality of wireless tags. The plurality of second wireless links are coupled to the first wireless link. In step 804, the first wireless link and the plurality of second wireless links are monitored to determine, in step 805, when one of the plurality of second wireless links has been lost to establish when a corresponding one of the plurality of products has been dispensed from the storage device.

Figure 9:
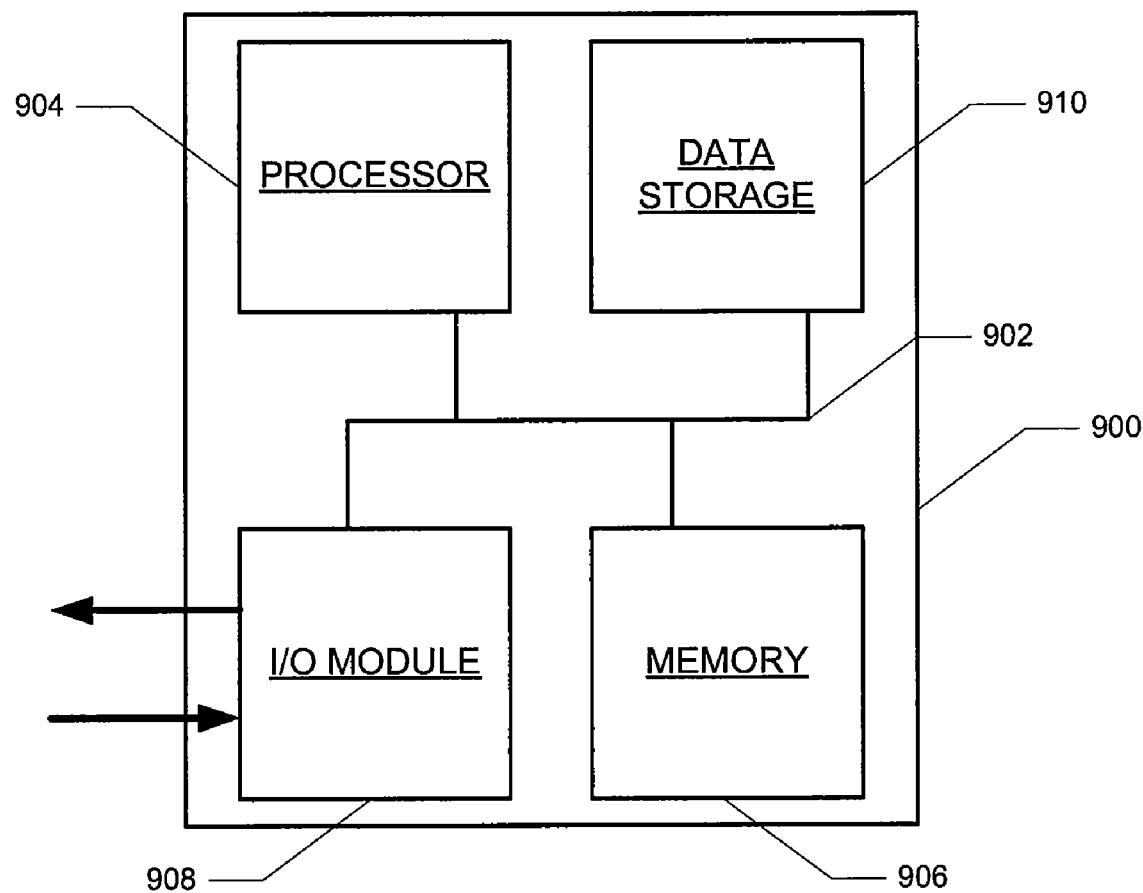
FIG. 9 is a block diagram that illustrates a computer system upon which certain embodiments may be implemented.

FIG. 9 is a block diagram that illustrates a computer system 900 upon which an embodiment may be implemented. Computer system 900 includes a bus 902 or other communication mechanism for communicating information, and a processor 904 coupled with bus 902 for processing information. Computer system 900 also includes a memory 906, such as a random access memory ("RAM") or other dynamic storage device, coupled to bus 902 for storing information and instructions to be executed by processor 904. Memory 906 may also be used for storing temporary variable or other intermediate information during execution of instructions to be executed by processor 904. Computer system 900 further includes a data storage device 910, such as a magnetic disk or optical disk, coupled to bus 902 for storing information and instructions.

Computer system 900 may be coupled via I/O module 908 to a display device (not illustrated), such as a cathode ray tube ("CRT") or liquid crystal display ("LCD") for displaying information to a computer user. An input device, such as, for example, a keyboard or a mouse may also be coupled to computer system 900 via I/O module 908 for communicating information and command selections to processor 904.

According to one embodiment of the invention, sensing the dispensation of a product from a storage device is performed by a computer system 900 in response to processor 904 executing one or more sequences of one or more instructions contained in memory 906. Such instructions may be read into memory 906 from another machine-readable medium, such as data storage device 910. Execution of the sequences of instructions contained in main memory 906 causes processor 904 to perform the process steps described herein. One or more processors in a multi-processing arrangement may also be employed to execute the sequences of instructions contained in memory 906. In alternative embodiments, hard-wired circuitry may be used in place of or in combination with software instructions to implement the invention. Thus, embodiments of the invention are not limited to any specific combination of hardware circuitry and software.

The term "machine-readable medium" as used herein refers to any medium that participates in providing instructions to processor 904 for execution. Such a medium may take many forms, including, but not limited to, non-volatile media, volatile media, and transmission media. Non-volatile media include, for example, optical or magnetic disks, such as data storage device 910. Volatile media include dynamic memory, such as memory 906. Transmission media include coaxial cables, copper wire, and fiber optics, including the wires that comprise bus 902. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention. For example, while the dispensation-sensing system has been described with reference to medical applications, wireless tags may be applied to any type of product, whether or not medical in nature, to provide automated and accurate dispensation sensing and tracking.

There may be many other ways to implement the invention. Various functions and elements described herein may be partitioned differently from those shown without departing from the sprit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the invention, and are not referred to in connection with the interpretation of the description of the invention. All structural and functional equivalents to the elements of the various embodiments described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A method of sensing dispensation of a product from a storage device having an antenna, the method comprising the steps of:
   providing a first product with a first wireless tag within a service area of the antenna;
   establishing wireless communication between the first wireless tag and the antenna, comprising:
      establishing a first wireless link between the first wireless tag of the first product and a second wireless tag of a second product; and
      establishing a second wireless link between the second wireless tag and the antenna;
   monitoring the wireless communication; and
   determining, responsive to the monitoring, when the wireless communication has ceased to establish when the first product has been dispensed from the storage device,
   wherein each of the first wireless tag and the second wireless tag is at least one of a radio frequency identification (RFID) tag, Bluetooth tag, or near field communication (NFC) tag.

2. The method of claim 1, wherein the step of establishing wireless communication includes:
   establishing a wireless link between the first wireless tag and the antenna.

3. The method of claim 1, wherein the step of monitoring the wireless communication includes monitoring the first wireless link.

4. The method of claim 1, wherein the step of establishing wireless communication includes:
   establishing a network of wireless links between a plurality of wireless tags;
   establishing a first wireless link between the first wireless tag of the first product and a first one of the plurality of wireless tags; and
   establishing a second wireless link between a second one of the plurality of wireless tags and the antenna.

5. The method of claim 4, wherein the step of monitoring the wireless communication includes monitoring the first wireless link.

6. The method of claim 4, wherein the network of wireless links utilize a first frequency, and wherein the second wireless link utilizes a second frequency.

7. The method of claim 4, wherein the network of wireless links utilize a first power level, and wherein the second wireless link utilizes a second power level higher than the first power level.

8. The method of claim 1, wherein the service area is located within the storage device.

9. The method of claim 1, wherein the first wireless tag is an active RFID tag.

10. The method of claim 1, wherein the first wireless tag includes a memory configured to store environmental information associated with the first product.

11. The method of claim 10, wherein the first wireless tag is operably coupled to one or more environmental sensors on the first product, and wherein the one or more environmental sensors provide the environmental information to the first wireless tag.

12. The method of claim 10, wherein the first wireless tag is configured to communicate the environmental information associated with the first product to the antenna.

13. The method of claim 12, wherein the storage device is operably coupled with a database, and wherein the environmental information associated with the first product is provided by the storage device to the database.

14. The method of claim 10, wherein the environmental information includes one or more of: a dispensation history of the first product, a temperature history of the first product, and a connectivity history of the first product to the first wireless tag.

15. The method of claim 1, further comprising the steps of:
   authenticating a user;
   permitting the user access to the storage device; and
   associating the user with the first product after the first product has been dispensed from the storage device.

16. The method of claim 15, wherein the storage device is operably coupled with a database, and wherein information about the user and the associated first product is provided by the storage device to the database.

17. A method of sensing dispensation of a product from a storage device having an antenna, the method comprising the steps of:
   providing a plurality of products within a service area of the antenna, each of the plurality of products including a wireless tag;
   establishing a first wireless link between the antenna and at least one of the plurality of wireless tags;
   establishing a plurality of second wireless links between the plurality of wireless tags, the plurality of second wireless links being coupled to the first wireless link;
   monitoring the first wireless link and the plurality of second wireless links; and
   determining, responsive to the monitoring, when one of the plurality of second wireless links has been lost to establish when a corresponding one of the plurality of products has been dispensed from the storage device,
   wherein the plurality of wireless tags comprise radio frequency identification (RFID) tags, Bluetooth tags, or near field communication (NFC) tags.

18. A dispensation-sensing system, comprising:
   a securable storage area;
   an antenna operable to receive and transmit signals within the securable storage area; and
   a processor configured to:
      establish wireless communication between the antenna and a first wireless tag of a first product disposed within the securable storage area, comprising:
         establish a first wireless link between the first wireless tag of the first product and a second wireless tag of a second product; and
         establish a second wireless link between the second wireless tag and the antenna;
      monitor the wireless communication, and
      determine, responsive to the monitoring, when the wireless communication has ceased to establish when the first product has been dispensed from the securable storage area,
   wherein the first wireless tag and the second wireless tag are at least one of a radio frequency identification (RFID) tag, Bluetooth tag, or near field communication (NFC) tag.

19. The dispensation-sensing system of claim 18, wherein the processor is further configured to collect environmental information about the first product from the first wireless tag.

20. The dispensation-sensing system of claim 19, further comprising a database operably coupled to the processor, wherein the processor is configured to provide the environmental information about the first product to the database.

21. The dispensation-sensing system of claim 18, wherein the processor is further configured to:

authenticate a user;

permit the user access to the storage device; and associate the user with the first product after the first product has been dispensed from the storage device.

22. The dispensation-sensing system of claim 21, further comprising a database operably coupled to the processor, wherein the processor is configured to provide the information about the user and the associated first product to the database.

23. The dispensation-sensing system of claim 18, wherein the processor is configured to monitor the wireless communication by monitoring the first wireless link.

24. The dispensation-sensing system of claim 18, wherein the processor is configured to establish wireless communication by establishing a network of wireless links between a plurality of wireless tags, establishing a first wireless link between the first wireless tag of the first product and a first one of the plurality of wireless tags, and establishing a second wireless link between a second one of the plurality of wireless tags and the antenna.

25. The dispensation-sensing system of claim 24, wherein the processor is configured to monitor the wireless communication by monitoring the first wireless link.

26. The dispensation-sensing system of claim 24, wherein the processor is further configured to monitor a topology of the network of wireless links to detect user activity.

* * * * *